United States Patent [19]
Wason et al.

[11] Patent Number: 5,747,008
[45] Date of Patent: May 5, 1998

[54] COST EFFECTIVE DENTAL COMPOSITIONS CONTAINING NOVEL SODIUM ALUMINOSILICATES

[75] Inventors: Satish K. Wason, Bel Air; James E. Sumpter, Aberdeen, both of Md.

[73] Assignee: J.M. Huber Corporation, Edison, N.J.

[21] Appl. No.: 778,655

[22] Filed: Jan. 3, 1997

Related U.S. Application Data

[62] Division of Ser. No. 297,181, Aug. 31, 1994, abandoned.

[51] Int. Cl.⁶ .................................................. A61K 7/16
[52] U.S. Cl. ........................... 424/52; 424/49; 423/339
[58] Field of Search ...................... 424/52, 49; 423/339

[56] References Cited

U.S. PATENT DOCUMENTS

| | | |
|---|---|---|
| 2,059,396 | 11/1936 | Ripert . |
| 3,424,602 | 1/1969 | Nauroth et al. . |
| 3,689,637 | 9/1972 | Pader . |
| 3,906,090 | 9/1975 | Colodney ................................ 424/52 |
| 3,911,102 | 10/1975 | Harrison . |
| 3,911,104 | 10/1975 | Harrison . |
| 3,928,541 | 12/1975 | Wason . |
| 3,977,893 | 8/1976 | Wason . |
| 3,988,162 | 10/1976 | Wason . |
| 4,015,996 | 4/1977 | Wason . |
| 4,036,949 | 7/1977 | Colodney . |
| 4,067,746 | 1/1978 | Wason et al. . |
| 4,076,549 | 2/1978 | Wason . |
| 4,105,757 | 8/1978 | Wason . |
| 4,122,161 | 10/1978 | Wason . |
| 4,144,322 | 3/1979 | Cordon et al. . |
| 4,340,583 | 7/1982 | Wason . |
| 4,420,312 | 12/1983 | Wason . |
| 4,421,527 | 12/1983 | Wason . |
| 5,108,734 | 4/1992 | Colodney et al. . |
| 5,110,574 | 5/1992 | Reinhardt et al. . |
| 5,124,143 | 6/1992 | Muhlemann et al. . |
| 5,512,271 | 4/1996 | McKeown et al. ...................... 424/52 |
| 5,543,014 | 8/1996 | Rushmere et al. ..................... 162/181 |

FOREIGN PATENT DOCUMENTS

| | | |
|---|---|---|
| 0 003 023 | 7/1979 | European Pat. Off. . |
| 0 098 641 | 1/1984 | European Pat. Off. . |
| 2 427 093 | 12/1979 | France . |
| 2 540 093 | 8/1984 | France . |
| 2 132 597 | 7/1984 | United Kingdom . |
| WO 86/02830 | 5/1986 | WIPO . |

*Primary Examiner*—Keith MacMillan

[57] ABSTRACT

Dental compositions comprise an abrasive, a humectant material, water and a binder. The abrasive comprises sodium aluminosilicate product having a water demand of greater than 50 g water per 100 g product, and the dental compositions comprise a water to abrasive weight ratio greater than 1.

9 Claims, No Drawings

COST EFFECTIVE DENTAL COMPOSITIONS CONTAINING NOVEL SODIUM ALUMINOSILICATES

This is a divisional of application Ser. No. 08/297,181 filed on Aug. 31, 1994 now abandoned.

FIELD OF THE INVENTION

The present invention relates to novel dental compositions containing sodium aluminosilicates (SAS), to novel sodium aluminosilicate abrasives and polishing agents, and to processes for the preparation of such products. More particularly, the present invention is directed to inexpensive dental compositions having good cleaning ability, which compositions contain novel sodium aluminosilicate abrasives and polishing agents, and to processes for preparation of such products.

BACKGROUND OF THE INVENTION

Modern-day toothpastes and dental formulations may be divided into two major categories: cosmetic types and therapeutic types. The cosmetic types do not contain anti-cavity ingredients such as fluoride while the therapeutic version, in-addition to other active ingredients, contain fluoride as an anti-carries agent. Toothpastes and dental formulations can also be further categorized into two additional categories, the classical toothpaste and the premium priced high humectant demand toothpaste.

The classical toothpaste typically contains an abrasive, a humectant and other ingredients. Typical examples of abrasives used in the classical toothpaste include alumina, di-calcium phosphate dihydrate (DCPD), insoluble sodium meta phosphate (IMP), calcium pyrophosphate, chalk (calcium carbonate) and related compounds. The classical toothpaste composition typically contains 40–50% of the above-mentioned abrasives and about 25% of a humectant such as glycerin and about 25% water. The abrasive, humectant and water system deliver an acceptable quality toothpaste to the marketplace. A typical classical toothpaste formula is given in Table I.

TABLE I

CLASSICAL TOOTHPASTE FORMULATION

| | |
|---|---|
| Dicalcium phosphate dihydrate (DCPD) | 40.00% |
| Anhydrous dicalcium phosphate | 5.00% |
| Sodium monofluorophosphate | 0.78% |
| Glycerin, 96% (humectant) | 25.00% |
| Carboxymethyl cellulose, grade 7MX | 1.00% |
| Sodium lauryl sulfate, dentifrice grade | 1.70% |
| Flavor | 2.00% |
| Sodium benzoate | 0.10% |
| Sodium saccharin | 0.30% |
| Water | 24.12% |

Around 1970, a new class of abrasive system was introduced which imparted transparent or translucent dentifrice properties, but also required high humectant levels in the compositions. The abrasive system in the high humectant demand toothpaste consisted of either silica gel or precipitated silica. A typical premium quality high humectant dentifrice composition containing a precipitated silica abrasive system is given in Table II.

TABLE II

PREMIUM, PRECIPITATED SILICA TOOTHPASTE FORMULATION

| | |
|---|---|
| Silica, precipitated (for abrasion) | 18.00% |
| Silica, precipitated (for thickening) | 4.00% |
| Sodium monofluorophosphate | 0.78% |
| Sorbitol, 70% solution (humectant) | 46.02% |
| Glycerin, 96% (humectant) | 20.90% |
| Polyethylene glycol 1450 | 5.00% |
| Carboxymethyl cellulose, grade 9MX | 0.30% |
| Sodium lauryl sulfate, dentifrice grade | 1.50% |
| Flavor | 1.00% |
| Sodium benzoate | 0.80% |
| Sodium saccharin | 0.20% |
| Color solution | 1.50% |

As can be seen from Table II, the silica abrasive system typically comprises about 20% of the formulation, while the humectant system comprises about 65% of the formulation, resulting in an approximate weight ratio of humectant to silica abrasives of 3 to 1. Examination of Table I shows that the ratio of humectant to the abrasive in the classical formulation is typically around 0.5. The humectants are rather expensive, and therefore the silica based premium quality high humectant demand toothpastes are more expensive to manufacture than their classical counterparts.

Toothpastes, both the classical type and the premium quality high humectant demand versions, are commonly sold commercially. However, there is a very significant need in the market for an inexpensive new generation toothpaste which requires a low level of humectant and has a very high water content. More particularly, in the western world, because of the high standard of living, it is quite common for toothpaste manufacturers to promote premium, high humectant silica-based toothpaste. However, in many parts of the world, especially in economically disadvantaged countries, there is a very strong need for a new generation toothpaste which requires lower levels of abrasives as compared with the classical toothpaste and having higher water demands and lower humectant demands as compared with the premium silica-based toothpaste, resulting in a low-cost formula.

SUMMARY OF THE INVENTION

Accordingly, it is an object of the present invention to provide novel dental compositions. It is a more specific object of the invention to provide novel dental compositions which are low in cost and which simultaneously provide good cleaning power. Additionally, it is an object of the invention to provide dental compositions having good appearance and good mouth feel, and having good therapeutic qualities. It is a further object of the invention to provide dental compositions which have low humectant demands and low abrasive contents and which contain high water contents. It is a related object of the invention to provide novel sodium aluminosilicate abrasives and polishing agents which are produced inexpensively and are suitable for use in preparing the novel dental compositions of the invention. Additionally, it is an object of the present invention to provide sodium aluminosilicate products having a high water demand and a low humectant demand. It is a further object of the invention to provide sodium aluminosilicate products which are compatible with other components of such dental compositions. It is a related object to provide inexpensive methods of preparing such sodium aluminosilicate compounds.

These and additional objects are provided by the present invention in the form of new dental compositions, new sodium aluminosilicate products, and processes for the production of such products. More particularly, the dental compositions according to the invention comprise an abrasive, a humectant material, water and a binder. The abrasive comprises sodium aluminosilicate (SAS) products having a water demand of greater than 50 g water per 100 g SAS product, and the dental compositions comprise a water to abrasive weight ratio greater than 1. Preferably, the novel sodium aluminosilicate compounds of the invention are of the formula $Na_2O \cdot Al_2O_3 \cdot 4XSiO_2 \cdot YH_2O$ wherein X is from about 2 to about 3.4 and Y is from about 2× to about 3×, and have a water demand of greater than about 50 g water per 100 g SAS product and less than about 90 g water per 100 g SAS product. It is additionally preferred that the sodium aluminosilicate product has a humectant demand less than about 80 g humectant per 100 g SAS product.

A process for producing the novel sodium aluminosilicate products according to the present invention comprises providing an aqueous solution of sodium sulfate and heating the solution, adding sodium silicate to the aqueous solution and when the pH of the aqueous solution reaches about 10.2, continuing the addition of the sodium silicate and initiating the addition of alum to the aqueous solution, continuing the addition of the sodium silicate and the alum to reduce the pH to about 8.4 and then reducing the addition rate of the alum to maintain the pH at about 8.5, completing the addition of the sodium silicate and then continuing the addition of the alum until the pH reaches about 5.9. The precipitated sodium aluminosilicate is allowed to digest to complete the reaction. Accordingly, the sodium aluminosilicate products may be inexpensively produced according to the methods set forth herein.

The present dental compositions provide a good combination of cleaning ability, therapeutic value, good appearance and good mouth feel. Additionally, owing to the low humectant levels, the low abrasive levels and the high water levels, the present dental compositions may be provided at a significantly lower cost than both the classical and the premium high-humectant formulations.

These and additional objects and advantageous of the dental compositions, sodium aluminosilicate products, and methods of the present invention will be more fully understood in view of the following detailed description.

DETAILED DESCRIPTION

Through a continued investigation, new generation dentifrice compositions have been discovered which employ a unique sodium aluminosilicate product as an abrasive system. The ratio of humectant to the abrasive in the present compositions is significantly lower than the ratio present in the premium high humectant silica-based dentifrice compositions. Additionally, the water to abrasive ratio is significantly higher in the present compositions as compared with both the classical and premium compositions. Thus, the new generation abrasive system is remarkable in that it is significantly lower in total system costs as compared with the silica-based composition and it has overcome the cost limitations of even the classical type toothpaste.

The dental compositions according to the present invention preferably comprise an abrasive, a humectant material, water and a binder. The abrasive comprises sodium aluminosilicate products having a water demand of greater than 50 g water per 100 g product, and the dental compositions comprise a water to abrasive weight ratio greater than 1. In a preferred embodiment, the dental compositions comprise from about 15 to about 35 weight percent of the abrasive, from about 10 to about 25 weight percent of the humectant material, from about 35 to about 70 weight percent water and from about 0.1 to about 5 weight percent of the binder. More preferably, the dental compositions comprise from about 20 to about 30 weight percent of the abrasive, from about 15 to about 23 weight percent of the humectant material, from about 40 to about 60 weight percent water and from about 0.5 to about 2 weight percent of the binder.

The humectant material which is included in the dental compositions of the present invention may be any of such materials known in the art and conventionally employed in dental compositions. In a preferred embodiment, the humectant material is selected from the group consisting of glycerine, sorbitol, xylitol, propylene glycol, corn syrup, glucose and mixtures thereof, with glycerine and sorbitol being particularly preferred.

The binder which is included in the dental compositions of the invention may similarly comprise any such materials known in the art and conventionally employed in dental compositions. Preferably, the binder is selected from the group consisting of alkali metal carboxymethyl celluloses, hydroxyethyl carboxymethyl celluloses, natural and synthetic gums, polyvinyl pyrrolidone, starch, water soluble hydrophilic colloidal carboxyvinyl polymers, seaweed colloids and mixtures thereof. In a more preferred embodiment, the binder comprises a carboxymethyl cellulose material.

The dental compositions of the present invention may provide a therapeutic effect by the inclusion therein of a fluoride-providing compound. In a preferred embodiment, the fluoride-providing compound comprises a monofluorophosphate salt, for example, sodium monofluorophosphate, lithium monofluorophosphate, potassium monofluorophosphate or mixtures thereof, or ammonium monofluorophosphate. The fluoride-providing compound is preferably included in the compositions in an amount of from about 0.1 to about 2.0 weight percent.

The dental compositions may further include one or more organic surface active agents or foaming agents in order to achieve increased distribution of the toothpaste composition during use, to assist in achieving thorough and complete dispersion of the composition throughout the oral cavity and to render the compositions more cosmetically acceptable. The organic surface active agent may be anionic, nonionic, ampholytic or cationic in nature. Examples of such agents include water-soluble salts of higher fatty acid monoglyceride monosulfates, higher alkyl sulfates, alkyl aryl sulfonates, olefin sulfonates, higher alkyl sulfoacetates and higher aliphatic acyl amides of lower aliphatic amino carboxylic acid compounds. These surface active agents may be used alone or in combination and in a preferred embodiment the total amount of surface active agents included in the compositions comprises from about 0.1 to about 5 weight percent.

The dental compositions may further include one or more ingredients including flavoring agents, coloring agents, whitening agents, preservatives, antibacterial agents and the like. Examples of suitable flavoring ingredients include flavoring oils, sweetening agents and the like. Preferably, these additional ingredients may each be included in an amount from about 0.1 to about 2 weight percent.

As noted above, the dental compositions according to the invention comprise a water to abrasive weight ratio of greater than 1. Thus, the compositions contain relatively greater amounts of water and less amounts of abrasive and humectant as compared with many conventional dentifrice compositions. The compositions of the invention are therefore significantly less expensive as compared with the conventional compositions.

Typical formulation costs are shown in Table III wherein the costs of a conventional classical formulation and a conventional premium high humectant demand formulation are set forth together with the costs of six dental formulations according to the invention. Specifically, the cost calculations for the various formulations were made based on the abrasive, humectant and water contents, which make up 94 kg per 100 kg of each formulation. The remaining 6 kg of the 100 kg of each formulation is made up of a combination of surface active agent, fluoride-providing compound, flavorings, sweeteners and preservatives which are assumed to be the same for each formulation, both in terms of content and cost. Thus, the cost calculations are based on the 94 kg per 100 kg of each formulation which vary from formulation to formulation. In calculating the costs of the various formulations, the following costs of materials in US dollars were employed, per kg of material:

| Ingredients | $/kg |
| --- | --- |
| DCPD (Abrasive) | 1.06 |
| Silica (Abrasive and thickener) | 1.17 |
| Sodium aluminosilicate (Invention) | 0.88 |
| Glycerine, 96% | 1.20 |
| Sorbitol, 70% solution | 0.53 |
| PEG | 1.34 |

TABLE IV

COST SAVINGS

| Formulation | Water: Abrasive Weight Ratio | Percent Savings Relative to Classical Formulation A |
| --- | --- | --- |
| A (Classical) | 0.53 | — |
| B (Premium) | 0.77* | — |
| C (Invention) | 1.4 | 33.6 |
| D (Invention) | 1.9 | 37.7 |
| E (Invention) | 1.1 | 29.5 |
| F (Invention) | 1.6* | 51.7 |
| G (Invention) | 2.1* | 56.7 |
| H (Invention) | 1.3* | 46.7 |

*The amount of water used in this determining this ratio included both added water and water if any in the humectant.

Thus, the dental compositions according to the present invention provide a significant cost savings.

The sodium aluminosilicate products of the present invention are prepared according to the following reaction sequence:

TABLE III

DENTAL FORMULATION COSTS

| Formulation | | DCPD | Silica | SAS | Glycerin | Sorbital | Water | PEG | Total kg | Cost per 94 kg, $ |
| --- | --- | --- | --- | --- | --- | --- | --- | --- | --- | --- |
| A (Classical) | kg,100 kg | 45 | — | — | 25 | — | 24 | — | 94 | 77.70 |
| | Cost, $ | 47.70 | — | — | 30.00 | — | — | — | | |
| B (Premium) | kg/100 kg | — | 22* | — | 21 | 46 | — | 5 | 94 | 82.00 |
| | Cost, $ | — | 25.74 | — | 25.20 | 24.38 | — | 6.70 | | |
| C (Invention) | kg/100 kg | — | — | 30 | 21 | — | 43 | — | 94 | 51.60 |
| | Cost, $ | — | — | 26.40 | 25.20 | — | — | — | | |
| D (Invention) | kg/100 kg | — | — | 25 | 22 | — | 47 | — | 94 | 48.40 |
| | Cost, $ | — | — | 22.00 | 26.40 | — | — | — | | |
| E (Invention) | kg/100 kg | — | — | 35 | 20 | — | 39 | — | 94 | 54.80 |
| | Cost, $ | — | — | 30.80 | 24.00 | — | — | — | | |
| F (Invention) | kg/100 kg | — | — | 30 | — | 21 | 43 | — | 94 | 37.50 |
| | Cost, $ | — | — | 26.40 | — | 11.10 | — | — | | |
| G (Invention) | kg/100 kg | — | — | 25 | — | 22 | 47 | — | 94 | 33.66 |
| | Cost, $ | — | — | 22.00 | — | 11.66 | — | — | | |
| H (Invention) | kg/100 kg | — | — | 35 | — | 20 | 39 | — | 94 | 41.40 |
| | Cost, $ | — | — | 30.80 | — | 10.60 | — | — | | |

*Comprises 18 kg silica abrasive and 4 kg silica thickener.

The cost savings of the formulations according to the present invention, formulations C–H, as compared with the cost of the classical formulation A in Table III are set forth in Table IV. To demonstrate the manner in which the savings were calculated, the cost savings achieved by formulation C according to the invention as compared with classical formulation A is calculated as follows: ((77.70−51.60)/77.70) ×100=33.6%. The water to abrasive weight ratios for each of formulations A–H in Table III are also set forth in Table IV. To demonstrate the manner in which the water to abrasive weight ratio is determined, this ratio for formulation F is as follows: (weight of added water+weight of water in humectant, if any)/weight of abrasive: (43 kg+(0.3×21 kg)) /30 kg=1.6.

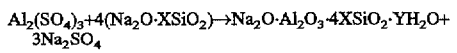

wherein X is from about 2 to about 3.4, more preferably from about 2.6 to about 3.3, and Y is from 2x to 3x. According to the specific process of the present invention, an aqueous solution of sodium sulfate is provided in a reactor. Agitation is provided and preferably the aqueous solution is heated. The heating may be maintained throughout the reaction sequence. Heating is suitably effected at a temperature of at least about 140° F. up to about 200° F., and more preferably at about 170°–195° F. Thus, the solution of sodium sulfate is preferably heated to a temperature of from about 170°–195° F. and maintained in this temperature range throughout the reaction.

The reaction is initiated by the addition of sodium silicate to the aqueous solution. Preferably the sodium silicate is added in the form of an aqueous solution and contains a $SiO_2/Na_2O$ molar ratio of X as defined above. Once the pH of the aqueous solution reaches about 10.2, the addition of the sodium silicate is continued and the addition of alum ($Al_2(SO_4)_3 \cdot H_2O$) to the aqueous solution is initiated. The alum is preferably purified and is added in the form of an aqueous solution. In a preferred embodiment, the sodium silicate solution and the alum solution are both heated prior to addition to the aqueous solution in the reaction. For example, the sodium silicate solution and the alum solution are heated to a temperature of about 120° F.

The additions of the sodium silicate and the alum are continued until the pH of the aqueous solution is reduced to about 8.4. The addition rate of the alum is then reduced in order to maintain the pH of the aqueous solution mixture at about 8.5. The addition of the sodium silicate is then completed and the addition of the alum to the aqueous solution is continued until the pH of the solution reaches about 5.9. Once the pH of the aqueous solution is reduced to about 5.9, the alum addition is discontinued. The precipitated sodium aluminosilicate product is then allowed to digest.

The resulting digested mixture containing a sodium aluminosilicate product may be filtered and the collected cake of precipitated sodium aluminosilicate product may be washed to remove sodium sulfate. In a preferred embodiment, the washed wet cake is then diluted slightly to fluidize the cake and the resulting cake slurry is dried, for example, to a moisture content of approximately 5%. Depending on the end use of the product, the product may then be milled to reduce the particle size. For example, when the sodium aluminosilicate product is to be used in a dental formulation, the dried product is milled to reduce its particle size to an average particle size of about 9 microns as measured using the Microtrac method described in the examples.

The sodium silicate and the alum are added to the reaction mixture in total amounts which provide a sodium aluminosilicate product of the formula $Na_2O \cdot Al_2O_3 \cdot 4XSiO_2 \cdot YH_2O$ wherein X is from about 2 to about 3.4 and Y is from about 2x to about 3x.

The process set forth above demonstrates that the sodium aluminosilicate products according to the present invention may be easily prepared, with relatively short production times and low expenses required for preparation of the products.

The sodium aluminosilicate products of the invention have a high water demand so that when they are used in dental compositions, the compositions can include relatively high water levels and relatively low humectant levels. For example, in a preferred embodiment, the sodium aluminosilicate products of the present invention have a water demand of greater than about 50 g water per 100 g product. Preferably, the products have a water demand upper limit of about 90 g water per 100 g product. The sodium aluminosilicate products preferably have a low humectant demand of less than about 80 g humectant per 100 g product. Additionally, the sodium aluminosilicate products have a relatively large pore volume, for example, a total pore volume of greater than about 1.40 as measured by the mercury intrusion method. The sodium aluminosilicate products of the present invention are further advantageous in that they are compatible with fluoride-providing materials such as monofluorophosphates. This further highlights the advantages of the use of sodium aluminosilicate products in dental formulations.

The following examples demonstrate the sodium aluminosilicate products and dental compositions of the present invention. Unless otherwise indicated, all parts and percentages set forth in the examples and throughout the present specification are by weight.

EXAMPLE 1

This example demonstrates the production of sodium aluminosilicate products according to the present invention.

To a 30 gallon reactor is added 30 liters of a 10–15% solution of $Na_2SO_4$. This solution is continuously agitated and heated to 190° F.±5 which temperature is maintained throughout the reaction. Agitation is also continued throughout the reaction. The reaction is initiated by the addition of a 20–22% sodium silicate solution (heated to about 120° F.) for exactly one minute at a rate of one liter per minute. The sodium silicate has a $SiO_2/Na_2O$ molar ratio of 2.65. After one minute a 40–48% alum ($Al_2(SO_4)_3 \cdot H2O$) solution heated to a temperature of about 120° F. is also added at a rate of 0.4 liter per minute. The pH of the reaction medium at this point is approximately 10.2. As the silicate and alum addition continues, the pH of the reaction declines to about 8.4 in approximately 10 minutes. At this point, the alum rate is reduced to 0.3 liter per minute to hold the reaction pH at 8.5.

After a total silicate addition time of 43 minutes has passed, the silicate flow is stopped. The alum addition continues until the reaction pH has declined to 5.9±0.1. At this point, the alum addition is stopped. The reaction is allowed to digest for 15 minutes to allow for a complete reaction.

The reaction slurry is filtered and washed to remove $Na_2SO_4$ by-product. The cake slurry is spray dried to a moisture content of approximately 5% and milled to reduce the particle size to about 9 micron (average particle size).

The resulting sodium aluminosilicate product was subjected to physical and chemical analysis, the results of which were as follows:

| Physical Properties: | |
| --- | --- |
| Oil Absorption, cc/100 g | 68 |
| Surface Area, m²/g | 43 |
| Brightness | 97.2 |
| Average Particle Size, micron | 8.94 |
| Bulk Density, lb/ft³ | 38.4 |
| Chemical Analysis: | % |
| $Na_2O$ | 4–7 |
| $Al_2O_3$ | 9–13 |
| $SiO_2$ | 66–76 |
| Hydrated Water | Balance |

The product was also determined to have a water demand of 64.9 g water per 100 g. Using the mercury intrusion volume method, the product was determined to have a high pressure pore volume of 1.3152, a low pressure pore volume of 0.1546 and a total pore volume of 1.47. The pore radius was measured as 5,000 Å. These values are compared with those of conventional abrasives used in known dental formulations in Tables V and VI.

TABLE V

| Abrasive | Water Demand (H$_2$O Per 100 g Abrasive) |
| --- | --- |
| DCPD | 23.3 |
| DCP (Anhydrous) | 19.4 |
| CaCO$_3$ | 33.7 |
| Al$_2$O$_3$ (Abrasive) | 20.5 |
| SAS (Of Present Invention) | 64.9 |

TABLE VI

| Abrasive | Bulk Density (lb/ft$^3$) | Total Hg Pore Volume (cc/g) | Hg Pore Radius (Å) | Surface Area BET (M$^2$/g) | Average Particle Size (µ) |
| --- | --- | --- | --- | --- | --- |
| DCPD | 69.4 | 0.63 | 14,000 | 3 | 13.07 |
| DCP (Anhy) | 96.0 | 0.41 | 11,000 | 2 | 15.25 |
| SAS (Invention) | 38.4 | 1.47 | 5,000 | 43 | 8.9 |

In the present specification, oil absorption is measured using the ASTM rub-out method D281. Surface area is determined by the BET nitrogen adsorption method of Brunaur et al, *J. Am. Chem. Soc.*, 60, 309 (1938). To measure brightness, fine powder materials that are pressed into a smooth surfaced pellet are evaluated using a Technidyne Brightimeter S-5/BC. This instrument has a dual beam optical system where the sample is illuminated at an angle of 45°, and the reflected light viewed at 0°. it conforms to TAPPI test methods T452 and T646, and ASTM Standard D985. A series of filters direct the reflected light of desired wavelengths to a photocell where it is converted to an output voltage. This signal is amplified and then processed by an internal microcomputer for display and printout.

The average particle size is measured using a Microtrac II apparatus, Leeds and Northrup. Specifically, a laser beam is projected through a transparent cell which contains a stream of moving particles suspended in a liquid. Light rays which strike the particles are scattered through angles which are inversely proportional to their sizes. The photodetector array measures the quantity of light at several predetermined angles. Electrical signals proportional to the measured light flux values are then processed by a microcomputer system to form a multi-channel histogram of the particle size distribution.

Bulk density is measured by noting the volume in liters occupied by a given weight of the abrasive, and is then reported in pounds per cubic foot.

Water demand and humectant demand are determined as follows: The procedure uses a Spex Mill (Spex Industries, Inc., #8000 Mixer Mill) which imparts a wrist action non shear motion to the materials being tested. Suitable test jars have a 125 ml capacity. The test is conducted by simply weighing sample into the test jar, adding the test liquid, and shaking in the Spex Mill. Sample weights are measured to 0.01 g accuracy and vary with the sample being tested. The test jar should be about half full and typical weights are from 5 to 10 grams. Addition of the liquid to the powder is facilitated by making a small hole in the powder, pouring the liquid into it, and covering it with dry powder from the sides. This prevents liquid from sticking to the sides of the jar and the lid while shaking. An equal weight of liquid and sample are added to the jar and the sample is shaken on the Spex Mill for 30 seconds. This represents 50% carrying capacity as a starting point. If a noticeable amount of liquid adheres to the sides of the jar, it should be scraped off with a spatula prior to adding additional liquid. The sample is observed to confirm that all of the liquid has in fact been taken into the sample. More liquid is then added to the same jar and the mixture shaken for an additional 30 seconds. This procedure is repeated until one observes a condition where a mixture of dry powder and wet lumps or granules has resulted. Small increments of liquid are added at this point (about 0.3 to 0.5 grams). The mixture will gradually change from powder and lumps to a condition where all of the powder has disappeared. This represents the endpoint and has the appearance of "play dough". The endpoint is a condition where the sample has been completely saturated and the resulting mixture becomes sticky to the touch. The weight of added liquid water or humectant, is used to calculate the water or humectant demand, respectively, per 100 g sample. Commonly employed humectants used in the present invention are glycerine and sorbitol.

The pore volumes (mercury pore volumes) are determined using an Autoscan 60 Porosimeter (Quantachrome Corporation). This instrument measures the void volume and pore size distribution of various materials. Mercury is forced into the voids as a function of pressure and the volume of mercury intruded per gram of sample is calculated at each pressure setting. Total pore volume expressed herein represents the cumulative volume of mercury intruded at pressures from vacuum to 60,000 psi. Increments in volume (cc/g) at each pressure setting are plotted against the pore radius corresponding to the pressure setting increments. The peak in the intruded volume versus pore radius curve corresponds to the mode in the pore size distribution. It identifies the most common pore size in the sample.

EXAMPLE 2

This example demonstrates dental compositions according to the present invention. The components included in each composition are set forth in Table VII together with the amount in which each component was included in the respective composition in parts by weight.

TABLE VII

DENTAL FORMULATIONS

| Composition | 1 | 2 | 3 | 4 | 5 | 6 |
| --- | --- | --- | --- | --- | --- | --- |
| Sorbitol (70.0% soln.) | 20.00 | 20.00 | 20.00 | — | — | — |
| Glycerine (99.5% soln.) | — | — | — | 20.00 | 20.00 | 20.00 |
| CMC-7MXF | 1.00 | 1.00 | 1.30 | 1.00 | 1.00 | 1.30 |
| Deionized H$_2$O | 40.95 | 40.19 | 45.65 | 40.95 | 40.19 | 45.65 |
| Abrasive | 35.00 | 35.00 | 30.00 | 35.00 | 35.00 | 30.00 |
| MFP | — | 0.76 | — | — | 0.76 | — |
| Preservative, Sweetener, Flavor, Whitener, Surface Active Agent | 3.05 | 3.05 | 3.05 | 3.05 | 3.05 | 3.05 |

The abrasive employed in these compositions comprises sodium aluminosilicate prepared generally in accordance with the methods set forth in Example 1. In Compositions 1–3, the humectant comprises sorbitol used in the form of a 70% solution. In Compositions 4–6, the humectant comprises glycerine employed in a 99.5% solution. In each of Compositions 1–6, the binder comprises a carboxymethyl cellulose (CMC-7MXF). As set forth in Table VII, Compositions 2 and 5 include a monofluorophosphate compound (MFP) to provide therapeutic value to the compositions. Additionally each of the compositions includes a combination of preservative, sweetener, flavoring agent, whitener and surface active agent which combined constitute 3.05 parts by weight of the compositions. The compositions set forth in this example clean well and have a good appearance, including good stand up and sheen. The compositions also exhibit a pleasing texture and mouth feel. The compositions are advantageous in that the abrasive is relatively inexpensive to manufacture and the compositions have a relatively high water demand and a low humectant demand, thereby providing a relatively inexpensive product. Additionally, as demonstrated by Compositions 2 and 5, these compositions have good compatibility with monofluorophosphate compounds.

EXAMPLE 3

This example further demonstrates dental compositions according to the present invention as set forth in Table VIII. Specifically, formulations 7–9 are according to the invention, while formulation 10 represents a classical dental formulation as discussed above including dicalcium phosphate as the abrasive. In the formulations according to the present invention, the abrasive content of the compositions was varied from 25 weight percent to 35 weight percent. The various measured properties of the formulations employed in this example are set forth in Table IX.

TABLE VIII

DENTAL FORMULATION

| Composition | 7 | 8 | 9 | 10 |
| --- | --- | --- | --- | --- |
| Glycerine (99.5% Soln.) | 20.00 | 20.00 | 20.00 | 22.00 |
| CMC - 7MXF | 1.80 | 1.30 | 1.00 | 1.20 |
| Deionized H$_2$O | 49.35 | 44.85 | 40.15 | 28.39 |
| Abrasive - Sodium Aluminosilicate | 25.00 | 30.00 | 35.00 | — |
| Abrasive - Dicalcium Phosphate | — | — | — | 45.00 |
| MFP | 0.76 | 0.76 | 0.76 | 0.76 |
| Preservative, Sweetener, Flavor, Whitener, Surface Active Agent | 3.09 | 3.09 | 3.09 | 2.65 |

TABLE IX

DENTAL FORMULATION PROPERTIES

| Composition | MFP % F Availability | RDA* | PCR** (Cleaning) |
| --- | --- | --- | --- |
| 7 | 97 | 99 | 86 |
| 8 | 94 | 109 | 114 |
| 9 | 96 | 116 | 117 |
| 10 | 97 | 65 | 76 |

*Radioactive Dentin Abrasion
**Pellicle Cleaning Ratio

Thus, the dental compositions of the invention have good abrasion and cleaning properties. Preferably, the present dental compositions have RDA values of at least 80 and more preferably at least 90, and PCR values of at least 75 and more preferably at least 80.

Within the present specification, fluoride availability is determined using a soluble fluoride method. In this method, the toothpaste compositions are stored for a specified length of time and temperature in a laminate tube. Thereafter, 10 grams of the composition are placed in a 10 ml beaker and then 45.0 grams of distilled water are added. The mixture is stirred to form a slurry in which the toothpaste is uniformly dispersed. The slurry is subsequently centrifuged for 10 minutes at 15,000 rpm or until the supernatant is clear. Then 10 ml of the supernatant is pipetted into a plastic vial. Thereafter, 5 ml of 2 molar perchloric acid is likewise pipetted into the plastic vial. The vial is capped, mixed and allowed to stand at room temperature for 24 hours. Then 25 ml of 1.5 molar sodium citrate buffer is pipetted into the vial. The sodium citrate buffer is prepared by dissolving 220.6 grams of sodium citrate in 500 ml of distilled water. A magnetic stir bar is added and gentle stirring is initiated. The fluoride ion concentration is determined by direct potentiometry with an Orion fluoride electrode (Model 95-09) to determine parts per million (ppm) fluoride in the supernatant. The fluoride availability value is then calculated by expressing the measured ppm soluble fluoride, as a percentage of the theoretically available soluble fluoride.

The RDA (radioactive dentin abrasion) values are determined according to the method set forth by Hefferren, *Journal of Dental Research*, July–August 1976, pp 563–573, and described in the Wason U.S. Pat. Nos. 4,340,583, 4,420,312 and 4,421,527, which publication and patents are incorporated herein by reference.

The PCR (Pellicle Cleaning Ratio) cleaning values are determined as follows:

Bovine, permanent, central incisors were cut to obtain labial enamel specimens approximately 10×10 mm. The enamel specimens were then embedded in an autopolymerizing methacrylate resin so that only the enamel surfaces were exposed. The enamel surfaces were then smoothed and polished on a lapidary wheel and lightly etched to expedite stain accumulation and adherence. They were placed on a rotating rod (in 37° C. incubator) alternately exposing them to air and to a solution consisting of trypticase soy broth, tea, coffee, mucin, FeCl$_3$, and Sarcina lutea.

The staining broth was changed and specimens rinsed twice daily for four days. After four days, a darkly-stained pellicle film was apparent on the enamel surfaces. Specimens were then rinsed, allowed to air dry, and refrigerated until use. All products were tested using specimens prepared at the same time.

The amount of in vitro stain was graded photometrically (Minolta C221, calorimeter) using only the L value of the LAB scale. The area of the specimens scored was a ¼ inch diameter circle in the center of the 10×10 mm enamel. Specimens with scores between 25–40 (25 being more darkly stained) were used. On the basis of these scores, the specimens were divided into groups of 8 specimens each, with each group having the same average baseline score.

The specimens were then mounted on a mechanical V-8 cross-brushing machine equipped with soft nylon-filament (Oral-B 40) toothbrushes. Tension on the enamel surface was adjusted to 150 g. The dentifrices were used as slurries prepared by mixing 25 grams of dentifrice with 40 ml of deionized water. The ADA reference material was prepared by mixing 10 g of material and 50 ml of a 0.5% CMC solution. The specimens were brushed for 800 strokes (4½ minutes). To minimize mechanical variables, one specimen per group was brushed on each of the eight brushing heads. Fresh slurries were made after being used to brush four teeth. Following brushing, specimens were rinsed, blotted dry, and scored again for stain as previously described. The study was then repeated with a second set of eight specimens in each group for a total group N of 16.

The difference between the pre- and post-brushing stain scores was determined and the mean and standard error calculated for the reference group in each study.

The cleaning ratio for the two reference material groups (one in each study) was assigned a value of 100. The mean decrement for each reference group was divided into 100 to obtain a constant value to multiple times each individual test decrement within each study. The individual cleaning ratio of each specimen was then calculated (decrement×constant). The mean and SEM for each group (N=16) was then calculated using the individual cleaning ratios. The larger the value of the cleaning ratio, the greater the amount of stained pellicle removed in this test.

Statistical analysis of the individual means was performed using the Bartlett Chi-square test for homogeneity of variance (at a=0.10). Since the homogeneity of variance could be assumed, the ANOVA was used to determine significant differences. A significant "F" value was indicated, so the Student Newman Keuls (SNK) test was used to determine statistically significant differences among the individual means.

The preceding examples are set forth to illustrate specific embodiments of the invention and are not intended to limit the scope of the compositions and methods of the present invention. Additional embodiments and advantageous within the scope of the claimed invention will be apparent to one of ordinary skill in the art.

We claim:

1. A dental composition, comprising an abrasive, a humectant material, water and a binder, the abrasive comprising sodium aluminosilicate of the formula $Na_2O \cdot Al_2O_3 \cdot 4XSiO_2 \cdot YH_2O$ wherein X is from about 2 to about 3.4 and Y is from about 2x to 3x, said sodium aluminosilicate having a water demand of greater than 50 g water per 100 g product, said water demand being defined as the weight of water required to saturate 100 g of said sodium aluminosilicate in dry powder form, and said dental composition comprising a water to abrasive weight ratio greater than 1.

2. A dental composition as defined by claim 1, comprising from about 15 to about 35 weight percent of the abrasive, from about 10 to about 25 weight percent of the humectant material, from about 35 to about 70 weight percent water and from about 0.1 to about 5 weight percent of the binder.

3. A dental composition as defined by claim 2, comprising from about 20 to about 30 weight percent of the abrasive, from about 15 to about 23 weight percent of the humectant material, from about 40 to about 60 weight percent water and from about 0.5 to about 2 weight percent binder.

4. A dental composition as defined by claim 1, wherein the humectant material is selected from the group consisting of glycerine, sorbitol, xylitol, propylene glycol, corn syrup, glucose and mixtures thereof.

5. A dental composition as defined by claim 1, wherein the binder is selected from the group consisting of alkali metal carboxymethyl celluloses, hydroxyethyl carboxymethyl celluloses, natural and synthetic gums, polyvinyl pyrrolidone, starch, water soluble hydrophilic colloidal carboxyvinyl polymers, seaweed colloids and mixtures thereof.

6. A dental composition as defined by claim 1, further comprising at least one additive selected from the group consisting of fluoride-providing compounds, flavoring agents, coloring agents, whitening agents, preservatives, foaming agents and antibacterial agents.

7. A dental composition as defined by claim 6, wherein the at least one additive is added in an amount of from about 0.1 to about 2 weight percent.

8. A dental composition as defined by claim 1, having an RDA value of at least 80.

9. A dental composition as defined by claim 1, having a PCR value of at least 75.

* * * * *